(12) United States Patent
Thomson et al.

(10) Patent No.: US 7,592,490 B2
(45) Date of Patent: Sep. 22, 2009

(54) PROCESS FOR PRODUCING ZINC DIALKYLDITHIOPHOSPHATES EXHIBITING IMPROVED SEAL COMPATIBILITY PROPERTIES

(75) Inventors: Paul M. Thomson, St. Louis, MS (US); Peter Growcott, Hartley Wintney (GB); Roger M. Sheets, Glen Allen, VA (US); Abbas Kadkhodayan, Collinsville, IL (US); Christopher James Dudding, Reading (GB)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 11/866,106

(22) Filed: Oct. 2, 2007

(65) Prior Publication Data

US 2008/0026966 A1    Jan. 31, 2008

Related U.S. Application Data

(62) Division of application No. 10/702,808, filed on Nov. 6, 2003, now Pat. No. 7,368,596.

(51) Int. Cl.
*C07F 9/02* (2006.01)
(52) U.S. Cl. .......................................................... 568/14
(58) Field of Classification Search ........................ None
See application file for complete search history.

(56) References Cited

U.S. PATENT DOCUMENTS

| | | | |
|---|---|---|---|
| 2,494,332 A | 1/1950 | Cyphers | |
| 2,680,123 A | 6/1954 | Mulvany | |
| 3,848,032 A | 11/1974 | La Suer | |
| 4,101,428 A | 7/1978 | Crawford | |
| 4,263,150 A | 4/1981 | Clason et al. | |
| 4,289,635 A | 9/1981 | Schroeck | |
| 4,308,154 A | 12/1981 | Clason et al. | |
| 4,392,966 A | 7/1983 | Schlicht | |
| 4,397,791 A | 8/1983 | Krause et al. | |
| 4,417,990 A | 11/1983 | Clason et al. | |
| 4,466,895 A | 8/1984 | Schroeck | |
| 4,786,423 A | 11/1988 | Schroeder | |
| 4,840,740 A | 6/1989 | Sato et al. | |
| 4,904,401 A | 2/1990 | Ripple et al. | |
| 4,943,672 A | 7/1990 | Hammer et al. | |
| 4,957,649 A | 9/1990 | Ripple et al. | |
| 5,154,844 A | 10/1992 | Perozzi | |
| 5,380,448 A | 1/1995 | Kadkhodayan et al. | |
| 5,384,054 A | 1/1995 | Kadkhodayan | |
| 5,726,132 A | 3/1998 | Roby et al. | |
| 5,728,656 A | 3/1998 | Yamaguchi et al. | |
| 5,750,477 A | 5/1998 | Sumiejski et al. | |
| 5,882,505 A | 3/1999 | Wittenbrink et al. | |
| 6,013,171 A | 1/2000 | Cook et al. | |
| 6,080,301 A | 6/2000 | Berlowitz et al. | |
| 6,096,940 A | 8/2000 | Writtenbrink et al. | |
| 6,103,099 A | 8/2000 | Writtenbrink et al. | |
| 6,114,288 A | 9/2000 | Fujitsu et al. | |
| 6,165,949 A | 12/2000 | Berlowitz et al. | |
| 6,180,575 B1 | 1/2001 | Nipe | |
| 6,300,291 B1 | 10/2001 | Hartley et al. | |

FOREIGN PATENT DOCUMENTS

| | | |
|---|---|---|
| DE | 197 53 961 | 10/1999 |
| EP | 0 131 400 | 1/1985 |
| EP | 0 666 264 | 8/1995 |
| EP | 0 866 113 | 9/1998 |
| GB | 716343 | 10/1954 |
| GB | 866502 | 4/1961 |
| GB | 1565961 | 4/1980 |
| JP | 52-102228 | 8/1977 |
| JP | 63-061090 | 3/1988 |
| JP | 7-285975 | 10/1995 |
| JP | 10-017885 | 1/1998 |
| JP | 10-273686 | 10/1998 |
| JP | 11-189782 | 7/1999 |
| JP | 11-302680 | 11/1999 |
| JP | 11-323370 | 11/1999 |

*Primary Examiner*—Daniel M Sullivan
*Assistant Examiner*—Yevegeny Valenrod
(74) *Attorney, Agent, or Firm*—MH2 Technology Law Group LLP

(57) ABSTRACT

In general terms, the present invention includes a process for producing a new zinc dialkyldithiophosphate (ZDDP) offering improved seal compatibility characteristics in engine and transmission oil packages. The present invention additionally includes zinc dialkyldithiophosphate produced in accordance with the disclosed methodologies, and oil additives, lubricants, and engines and transmission comprising the zinc dialkyldithiophosphate of the present invention.

10 Claims, No Drawings

PROCESS FOR PRODUCING ZINC DIALKYLDITHIOPHOSPHATES EXHIBITING IMPROVED SEAL COMPATIBILITY PROPERTIES

This is a division of application Ser. No. 10/702,808, filed Nov. 6, 2003 now U.S. Pat. No. 7,368,596 which is incorporated herein by reference.

TECHNICAL FIELD OF THE INVENTION

The present invention is in the field of engine and transmission oil packages. Specifically, the present invention provides a method for synthesizing zinc dialkyldithiophosphates that exhibit improved seal compatibility compared to the zinc dialkyldithiophosphates of the prior art.

BACKGROUND OF THE INVENTION

Presently in the field of engine and transmission oil packages, seal compatibility is an issue that formulators must consider in order to produce an acceptable product. As an engine oil package is a blend of several components, each offering various advantages and disadvantages to the blend, a formulator is limited in his ability to combine certain components if those components do not offset each others respective limitations. For instance, many dispersants offer seal compatibility properties to the blend, however, these dispersants do not possess the same level of dispersing characteristics as non-seal compatible dispersants. Therefore, if seal compatibility properties can be imbued into the blend via another component, the formulator may then use a more aggressive dispersant and thereby achieve an engine or transmission oil package offering superior performance over the prior lubricating oil packages.

It is a goal of the present invention to produce a seal friendly zinc dialkyldithiophosphate (ZDDP) so as to enable a formulator to use more aggressive dispersants in their formulations as the seal friendly dispersants previously employed have diminished dispersing characteristics by comparison.

In view of the present disclosure or through practice of the present invention, other advantages may become apparent.

SUMMARY OF THE EMBODIMENTS

In general terms, in one embodiment herein is presented a method for producing a thioacid and the thioacid so produced.

The present invention provides a method for producing a thioacid useful in the production of zinc dialkyldithiophosphate. The method comprises the steps of: (a) initiating a reaction by introducing a mixture of $P_2O_5$ and $P_2S_5$ to a solution comprising at least methyl isobutyl carbinol and isopropyl alcohol; (b) maintaining the reaction in a temperature range while adding the mixture of $P_2O_5$ and $P_2S_5$ to the solution comprising methyl isobutyl carbinol and isopropyl alcohol so as to form a slurry; (c) diluting the slurry by adding an additional quantity of the solution comprising methyl isobutyl carbinol and isopropyl alcohol so as to form a dilute slurry while maintaining the dilute slurry in the temperature range; and (d) maintaining the dilute slurry in the temperature in the range so as to form the thioacid.

In one embodiment the solution comprising methyl isobutyl carbinol and isopropyl alcohol is agitated when the mixture of $P_2O_5$ and $P_2S_5$ is added. In another embodiment the solution of methyl isobutyl carbinol and isopropyl alcohol is initially at a temperature in the range of from about 58° C. to about 68° C. Another temperature range can extend from about 86° C. to about 96° C.

The aforementioned method may optionally comprise the additional step of isolating the thioacid by filtering said dilute slurry.

In another embodiment the mixture of $P_2O_5$ and $P_2S_5$ comprises, on a weight basis, from about 35 to about 400 parts $P_2S_5$ to about 1 part $P_2O_5$. In yet another embodiment, the mixture of $P_2O_5$ and $P_2S_5$ comprises, on a weight basis, from about 56 to about 205 parts $P_2S_5$ to about 1 part $P_2O_5$.

In one embodiment, a catalyst is used to facilitate the reaction. In another embodiment, caprolactam is used as a catalyst for the reaction.

The solution comprising methyl isobutyl carbinol and isopropyl alcohol can be an equimolar solution of these components.

The present invention includes the thioacids produced in accordance with the above stated method.

The present invention also includes an alternative method for producing a thioacid useful in the production of zinc dialkyldithiophosphate. This method comprises the steps of: (a) initiating a reaction by introducing $P_2S_5$ into a first solution; (b) maintaining the reaction in a temperature range while continuing to add the $P_2S_5$ to the first solution so as to form a slurry; (c) diluting the slurry by adding an additional quantity of the first solution so as to form a dilute slurry while maintaining the dilute slurry in the temperature range; and (d) maintaining the dilute slurry in the temperature range so as to form the thioacid.

It is desirable that the first solution is agitated as the $P_2S_5$ is added. It is also possible that the first solution is initially at a temperature in the range of from about 58° C. to about 68° C. Another temperature range can extend from about 86° C. to about 96° C.

The first solution can, in one embodiment be formed, on a weight basis, by a method comprising the steps of: (a) creating a mixture comprising from about 35 parts to about 260 parts of methyl isobutyl carbinol to about 1 part $P_2O_5$; and (b) forming the first solution by adding 1 part isopropyl alcohol to from about 1.50 to about 1.90 parts of the mixture. In another embodiment the first solution can be formed, on a weight basis, by a method comprising the steps of: (a) creating a mixture comprising from about 53 parts to about 194 parts of methyl isobutyl carbinol to about 1 part $P_2O_5$; and (b) forming the first solution by adding 1 part isopropyl alcohol to from about 1.70 to about 1.74 parts of the mixture.

The aforementioned method may optionally comprise the additional step of isolating the thioacid by filtering said dilute slurry.

In one embodiment, a catalyst is used to facilitate the reaction. In another embodiment, caprolactam is used as a catalyst for the reaction.

The present invention includes the thioacids produced in accordance with the above stated method.

The present invention additionally provides a method for producing a zinc dialkyldithiophosphate solution comprising zinc dialkyldithiophosphate. This method comprises the steps of: (a) providing a thioacid; (b) sparging the thioacid with nitrogen until the thioacid tests negative for $H_2S$ with lead acetate paper (c) neutralizing the thioacid by dosing the thioacid into a zinc oxide slurry at a temperature within a first temperature range so as to form a reaction mixture; (d) maintaining the reaction mixture in a second temperature range while adding the thioacid; (e) holding the reaction mixture in the second temperature range for at least 45 minutes after adding the thioacid; (f) vacuum stripping the reaction mixture; (g) filtering the reaction mixture so as to remove any solid particles; and (h) diluting the reaction mixture with process oil thereby producing the zinc dialkyldithiophosphate solution.

It is desirable that the first temperature is a temperature in the range of from about 50° C. to about 70° C. Further, it is desirable that the second temperature range extend from about 78° C. to about 88° C.

In one embodiment, the zinc oxide slurry is formed, on a weight basis, by a method comprising the step of: adding 1 part of zinc oxide to from about 1.0 parts to about 1.3 parts of process oil so as to form the zinc oxide slurry. It is even more desirable that the zinc oxide slurry is formed, on a weight basis, by a method comprising the step of: adding 1 part of zinc oxide to from about 1.10 parts to about 1.16 parts of process oil so as to form the zinc oxide slurry.

An alternative method of the present invention for producing a solution of zinc dialkyldithiophosphate comprises the steps of: (a) initiating a reaction by introducing a mixture of $P_2O_5$ and $P_2S_5$ to a solution comprising methyl isobutyl carbinol and isopropyl alcohol; (b) maintaining the reaction in a temperature range while adding the mixture comprising $P_2O_5$ and $P_2S_5$ to said solution of methyl isobutyl carbinol and isopropyl alcohol so as to form a slurry; (c) diluting the slurry by adding an additional quantity of the solution comprising methyl isobutyl carbinol and isopropyl alcohol so as to form a dilute slurry while maintaining the dilute slurry in the temperature range; (d) maintaining the dilute slurry in the temperature range so as to form the thioacid; (e) sparging the thioacid with nitrogen until the thioacid tests negative for $H_2S$ with lead acetate paper; (f) neutralizing the thioacid by dosing the thioacid into a zinc oxide slurry so as to form a reaction mixture; (g) maintaining the reaction mixture in a second temperature range while adding the thioacid; (h) holding the reaction mixture in the second temperature range for at least 45 minutes after adding the thioacid; (i) vacuum stripping the reaction mixture; (j) optionally filtering the reaction mixture so as to remove any solid particles; and (k) optionally diluting the reaction mixture with process oil thereby producing the zinc dialkyldithiophosphate solution.

It is desirable that the solution comprising methyl isobutyl carbinol and isopropyl alcohol is agitated as the mixture of $P_2O_5$ and $P_2S_5$ is added. It is further preferred that the solution comprising methyl isobutyl carbinol and isopropyl alcohol is initially at a temperature in the range of from about 58° C. to about 68° C. Another temperature range can extend from about 86° C. to about 96° C. Finally, it is desirable that the second temperature range is from about 78° C. to about 88° C.

The aforementioned method may optionally comprise the additional step of isolating the thioacid by filtering said dilute slurry.

In one embodiment of the aforementioned method the mixture of $P_2O_5$ and $P_2S_5$ comprises, on a weight basis, from about 35 to about 400 parts $P_2S_5$ to about 1 part $P_2O_5$. Alternatively, in the aforementioned method the mixture of $P_2O_5$ and $P_2S_5$ comprises, on a weight basis, from about 56 to about 205 parts $P_2S_5$ to about 1 part $P_2O_5$.

In one embodiment, a catalyst is used to facilitate the reaction. In another embodiment, caprolactam is used as a catalyst for the reaction.

Also, the solution comprising methyl isobutyl carbinol and isopropyl alcohol can be an equimolar solution.

Additionally, it is desirable that the zinc oxide slurry is formed, on a weight basis, by a method comprising the step of (a) adding 1 part of zinc oxide to from about 1.0 parts to about 1.3 parts of process oil so as to form the zinc oxide slurry. In one embodiment, the zinc oxide slurry is formed, on a weight basis, by a method comprising the step of: (a) adding 1 part of zinc oxide to from about 1.10 parts to about 1.16 parts of process oil so as to form the zinc oxide slurry.

A second alternative method of the present invention for producing a solution of zinc dialkyldithiophosphate comprises the steps of: (a) initiating a reaction by introducing $P_2S_5$ into a first solution; (b) maintaining the reaction in a temperature range while continuing to add said $P_2S_5$ to said first solution so as to form a slurry; (c) diluting the slurry by adding additional first solution so as to form a dilute slurry while maintaining the dilute slurry in the temperature range; (d) maintaining the dilute slurry in the temperature range so as to form said thioacid; (e) sparging said thioacid with nitrogen until said thioacid tests negative for $H_2S$ with lead acetate paper; (f) neutralizing the thioacid by dosing the thioacid into a zinc oxide slurry at a temperature within an initial temperature range so as to form a reaction mixture; (g) maintaining the reaction mixture in a second temperature range while adding the thioacid; (h) holding the reaction mixture in the second temperature range for at least 45 minutes after adding the thioacid; (i) optionally vacuum stripping the reaction mixture; (j) optionally filtering the reaction mixture so as to remove any solid particles; and (k) optionally diluting the reaction mixture with process oil thereby producing the zinc dialkyldithiophosphate solution.

It is desirable that the first solution is agitated as the $P_2S_5$ is added to it. In one embodiment the first solution is initially at a temperature in the range of from about 58° C. to about 68° C. It is further desirable that the temperature range extends from about 86° C. to about 96° C. In another embodiment the second temperature range is from about 78° C. to about 88° C.

In one embodiment, a catalyst is used to facilitate the reaction. In another embodiment, caprolactam is used as a catalyst for the reaction.

It is desirable that the first solution in the aforementioned method is formed, on a weight basis, by a method comprising the steps of: (a) creating a mixture comprising from about 35 parts to about 260 parts of methyl isobutyl carbinol to about 1 part $P_2O_5$; and (b) forming the first solution by adding 1 part isopropyl alcohol to from about 1.50 to about 1.90 parts of the mixture. The first solution in the aforementioned method is formed, on a weight basis, by a method comprising the steps of (a) creating a mixture comprising from about 53 parts to about 194 parts of methyl isobutyl carbinol to about 1 part $P_2O_5$; and (b) forming the first solution by adding 1 part isopropyl alcohol to from about 1.70 to about 1.74 parts of the mixture.

The aforementioned method may optionally comprise the additional step of isolating the thioacid by filtering said dilute slurry.

In one embodiment, the zinc oxide slurry is formed, on a weight basis, by a method comprising the step of: (a) adding 1 part of zinc oxide to from about 1.0 parts to about 1.3 parts of process oil so as to form the zinc oxide slurry. In another embodiment, the zinc oxide slurry is formed, on a weight basis, by a method comprising the step of: (a) adding 1 part of zinc oxide to from about 1.10 parts to about 1.16 parts of process oil so as to form the zinc oxide slurry.

Irrespective of which method of the present invention is used for producing a solution of zinc dialkyldithiophosphate, the present invention also includes (a) the zinc dialkyldithiophosphate produced; (b) oil additive packages comprising the zinc dialkyldithiophosphate so produced; (c) lubricating oils comprising the zinc dialkyldithiophosphate so produced; (d) engines and/or transmissions lubricated with lubricating oils comprising the zinc dialkyldithiophosphate so produced; and (e) diesel and gasoline auto and truck engines and/or transmissions comprising the zinc dialkyldithiophosphate so produced.

DETAILED DESCRIPTION OF THE PREFERRED EMBODIMENT(S)

In accordance with the foregoing summary of the invention, the following presents a detailed description of the preferred embodiment of the invention which is presently considered to be its best mode.

In order to produce the zinc dialkyldithiophosphate of the present invention, a thioacid is neutralized. Although any thioacid may be used, preferred thioacids are produced in accordance with one of the following synthesis methods:

Thioacid Synthesis Method 1

From about 1.4 to 5.1 grams of $P_2O_5$ is added to about 287.5 grams of $P_2S_5$ in a round bottom flask and sealed. This mixture is slowly charged with 108 grams of an equimolar mixture of methyl isobutyl carbinol (MIBC) and isopropyl alcohol (IPA) at 60-65° C. under agitation. This is an exothermic reaction and the temperature should be maintained at 88-94° C. Although not required, caprolactam may be used as a catalyst. After all of the $P_2O_5$ and $P_2S_5$ mixture has been charged to the alcohol heel, 322 grams of the equimolar mixture of MIBC and IPA is added to the slurry over the course of two hours, maintaining a temperature of 88-94° C. The mixture is then held for one hour at the reaction temperature. After the one hour cook the thioacid may be filtered using filter paper.

Thioacid Synthesis Method 2

From about 1.4 to 5.1 grams of $P_2O_5$ are dissolved in 270.9 grams of MIBC. This mixture is then mixed with 159.4 grams of IPA. Next 287.5 grams of $P_2S_5$ are slowly charged with approximately 105 grams of the mixture of $P_2O_5$/MIBC/IPA at 60-65° C. under agitation. This is an exothermic reaction and the temperature should be maintained at 88-94° C. Although not required, caprolactam may be used as a catalyst. After all the $P_2S_5$ has been charged to the alcohol heel, approximately 325 grams of the $P_2O_5$/MIBC/IPA mixture is added to the slurry over the course of two hours, maintaining a temperature of 88-94° C. The mixture is then held for one hour at the reaction temperature. After the one hour cook, the thioacid may be filtered using filter paper.

Thioacid Neutralization (ZDDP Production)

Whether starting with a thioacid produced in accordance with one of the two aforementioned thioacid synthesis methods or a commercially available thioacid, the first step in zinc dialkyldithiophosphate production is to neutralize the thioacid. This is done by first creating a zinc oxide slurry in oil. Approximately, 110 grams of zinc oxide are added to 125 grams of process oil. The slurry is heated to 60° C. Next, 600 grams of the thioacid are then slowly dosed into the zinc oxide slurry over 80-100 minutes while agitating. An exotherm is initially observed and a reaction temperature of 80-84° C. should be maintained during the thioacid additional period. After all the thioacid has been charged, the reaction mixture is held for one hour at 82-84° C. When the one-hour cook is finished, the batch is vacuum stripped for thirty minutes. The reaction mixture is then filtered and diluted with process oil to give the finished product—the zinc dialkyldithiophosphate of the present invention.

Comparative Results

The following tables illustrate VW AK 6 505 test results, using test method PV3344—an industry recognized seals test.

For comparative purposes a standard ZDDP sample was used as a benchmark. The standard ZDDP sample was produced by slowly charging into a sealed round bottom flask containing 287.5 grams of $P_2S_5$ 108 grams of an equimolar mixture of methyl isobutyl carbinol (MIBC) and isopropyl alcohol (IPA) at 60-65° C. while agitating. This is an exothermic reaction and the temperature was maintained at 88-94° C. After all of the $P_2S_5$ has been charged to the alcohol heel, 322 grams of the equimolar mixture of MIBC and IPA was added to the slurry over the course of two hours, while maintaining a temperature of 88-94° C. The mixture was then held for one hour at the reaction temperature. After the one hour cook, the thioacid was filtered using filter paper. Next, the thioacid was neutralized with a zinc oxide slurry. The zinc oxide slurry was formed by adding approximately 110 grams of zinc oxide to 125 grams of process oil. The slurry was heated to 60° C. Next, 600 grams of the thioacid were then slowly dosed into the zinc oxide slurry over 80-100 minutes while agitating. An exotherm was initially observed and a reaction temperature of 80-84° C. was maintained during the thioacid addition period. After all the thioacid had been charged, the reaction mixture was held for one hour at 82-84° C. When the one-hour cook was finished, the batch was vacuum stripped for thirty minutes. The reaction mixture was then filtered and diluted with process oil to give the finished product—the standard zinc dialkyldithiophosphate (ZDDP) sample.

The table below compares the VW AK 6 505 test results for ZDDP samples prepared by adding $P_2O_5$ to $P_2S_5$ to the standard ZDDP sample.

| ZDDP Sample prepared by adding $P_2O_5$ to $P_2S_5$ | $P_2S_5:P_2O_5$ | Tensile Strength (8.0 min) | Elongation (160 min) | Hardness (Report) | Cracks (Y/N) | Pass/Fail |
|---|---|---|---|---|---|---|
| Sample 1 | 56 | 8.7 | 186 | 71 | N | Pass |
| Sample 2 | 56 | 9.1 | 193 | 74 | N | Pass |
| Sample 3 | 205 | 8.9 | 185 | 70 | N | Pass |
| Sample 4 | 205 | 8.4 | 176 | 71 | N | Pass |
| Standard ZDDP | NA | 7.3 | 142 | 73 | Y | Fail |

As evident from the table above, the inventive ZDDP samples pass the VW AK 6 505 test while the standard ZDDP does not.

The table below compares the VW AK 6 505 test results for ZDDP samples prepared by dissolving $P_2O_5$ in MIBC to the standard ZDDP sample.

| ZDDP Sample prepared by dissolving $P_2O_5$ in MIBC | $P_2S_5:P_2O_5$ | Tensile Strength (8.0 min) | Elongation (160 min) | Hardness (Report) | Cracks (Y/N) | Pass/Fail |
|---|---|---|---|---|---|---|
| Sample 1 | 53 | 9.2 | 181 | 71 | N | Pass |
| Sample 2 | 53 | 9.3 | 182 | 71 | N | Pass |
| Sample 3 | 53 | 9.5 | 8.7 | 70 | N | Pass |
| Sample 4 | 194 | 8.7 | 169 | 71 | N | Pass |
| Standard ZDDP | NA | 7.2 | 135 | 72 | Y | Fail |

As evident from the table above, the inventive ZDDP samples pass the VW AK 6 505 test while the standard ZDDP does not.

In conclusion, the ZDDP of the present invention exhibits improved seal compatibility as compared to the standard ZDDP sample thereby permitting a formulator to use more aggressive dispersants and thereby achieve an engine or transmission oil package offering superior performance over the prior lubricating oil packages.

In view of the present disclosure or through practice of the present invention, it will be within the ability of one of ordinary skill to make modifications to the present invention, such as through the use of equivalent arrangements and compositions, in order to practice the invention without departing from the spirit of the invention as reflected in the appended claims.

What is claimed is:

1. A method for producing a solution of zinc dialkyldithiophosphate, said method comprising the steps of:
   initiating a reaction by introducing a mixture of $P_2O_5$ and $P_2S_5$ to a solution comprising methyl isobutyl carbinol and isopropyl alcohol;
   maintaining said reaction in a temperature range of from about 58° C. to about 68° C.;
   adding said mixture of $P_2O_5$ and $P_2S_5$ to said solution comprising methyl isobutyl carbinol and isopropyl alcohol so as to form a slurry;
   diluting said slurry by adding an additional quantity of said solution comprising methyl isobutyl carbinol and isopropyl alcohol so as to form a dilute slurry while maintaining said dilute slurry in said temperature range;
   maintaining said dilute slurry in said temperature range so as to form a thioacid;
   sparging said thioacid with nitrogen until said thioscid tests negative for $H_2S$ with lead acetate paper;
   neutralizing said thioacid by dosing said thioacid into a zinc oxide slurry so as to form a reaction mixture;
   maintaining said reaction mixture in a second temperature range while adding said thioacid;
   holding said reaction mixture in said second temperature range for at least 45 minutes after adding said thioacid;
   optionally vacuum stripping said reaction mixture;
   optionally filtering said reaction so as to remove any solid particles; and
   optionally diluting said reaction mixture with process oil thereby producing said zinc dialkyldithiophosphate solution.

2. The method according to claim 1 additionally comprising the step of: isolating said thioacid by filtering said dilute slurry.

3. The method according to claim 1 wherein said reaction so as to form said thioacid is conducted in the absence of a catalyst.

4. The method according to claim 1 wherein said mixture of $P_2O_5$ and $P_2S_5$ comprises, on a weight basis, from about 35 to about 400 parts $P_2S_5$ to about 1 part $P_2O_5$.

5. The method according to claim 1 wherein said solution comprising methyl isobutyl carbinol and isopropyl alcohol is an equimolar solution of methyl isobutyl carbinol and isopropyl alcohol.

6. The method according to claim 1 wherein said zinc oxide slurry is formed, on a weight basis, by a method comprising the step of:

adding 1 part of zinc oxide to from about 1.0 parts to about 1.3 parts of process oil so as to form said zinc oxide slurry.

7. A method for producing a solution of zinc dialkyldithiophosphate, said method comprising the steps of:

initiating a reaction by introducing $P_2S_5$ into a first solution, wherein said first solution is formed, on a weight basis, by a method comprising the steps of:

creating a mixture comprising from about 35 parts to about 260 parts of methyl isobutyl carbinol to about 1 part $P_2O_5$; and forming said first solution by adding 1 part isopropyl alcohol;

maintaining said reaction in a temperature range while continuing to add said $P_2S_5$ to said first solution so as to form a slurry;

diluting said slurry by adding additional said first solution so as to form a dilute slurry while maintaining said dilute slurry in said temperature range;

maintaining said dilute slurry in said temperature range so as to form a thioacid;

sparging said thioacid with nitrogen until said thioacid tests negative for $H_2S$ with lead acetate paper;

neutralizing said thioacid by dosing said thioacid into a zinc oxide slurry so as to form a reaction mixture;

maintaining said reaction mixture in a second temperature range while adding said thioacid;

holding said reaction mixture in said second temperature range for at least 45 minutes after adding said thioacid;

optionally vacuum stripping said reaction mixture;

optionally filtering said reaction so as to remove any solid particles; and optionally diluting said reaction mixture with process oil thereby producing said zinc dialkyldithiophosphate solution.

8. The method according to claim 7 wherein said reaction is conducted in the absence of a catalyst.

9. The method according to claim 7 additionally comprising the step of:

isolating said thioacid by filtering said dilute slurry.

10. The method according to claim 7 wherein said zinc oxide slurry is formed, on a weight basis, by a method comprising the step of:

adding 1 part of zinc oxide to from about 1.0 parts to about 1.3 parts of process oil so as to form said zinc oxide slurry.

* * * * *